United States Patent [19]

Charlton et al.

[11] Patent Number: 4,839,299

[45] Date of Patent: Jun. 13, 1989

[54] ASSAY FOR THE FREE PORTION OF SUBSTANCES IN BIOLOGICAL FLUIDS

[75] Inventors: John C. Charlton; John E. Midgley; Terence A. Wilkins, all of Amersham, England

[73] Assignee: Amersham International plc., Little Chalfont, England

[21] Appl. No.: 75,254

[22] Filed: Jul. 17, 1987

Related U.S. Application Data

[63] Continuation of Ser. No. 748,702, Jun. 25, 1985, abandoned, which is a continuation of Ser. No. 475,113, Mar. 14, 1983, abandoned.

[30] Foreign Application Priority Data

Mar. 22, 1982 [GB] United Kingdom ............... 82-08273

[51] Int. Cl.$^4$ ................. G01N 33/567; G01N 33/566; G01N 33/53; B65D 69/00
[52] U.S. Cl. .................................... 436/500; 436/501; 436/504; 436/505; 436/800; 436/804; 436/815; 436/817; 422/61
[58] Field of Search ............... 436/500, 501, 504, 505, 436/800, 804, 815, 817; 422/61

[56] References Cited

U.S. PATENT DOCUMENTS

| 3,960,492 | 6/1976 | Di Giulio | 436/500 |
| 4,222,744 | 9/1980 | McConnell | 436/800 |
| 4,311,690 | 1/1982 | Buehler et al. | 424/1.1 |
| 4,366,143 | 12/1982 | Midgley et al. | 436/504 |
| 4,426,453 | 1/1984 | Greg et al. | 436/542 |

FOREIGN PATENT DOCUMENTS

| 26103 | 4/1981 | European Pat. Off. | 436/500 |
| 3306 | 9/1983 | World Int. Prop. O. | 436/500 |

OTHER PUBLICATIONS

Ekins, "Free Hormones in Blood", Elsevier Biomedical Press (1982), pp. 73–90.
Ekins, "The Direct Immunoassay of Free (Non-Protein Bound), Hormones in Body Fluids", pp. 192–219.
"Radioimmunoassay and Related Procedures in Medicine", IAEA, Vienna (1982), pp. 191–219.
Miles et al, from Principles of Competitive Protein—Binding Assays, Eds. Odell et al, J. B. Lippincott Co., Philadelphia, 1971, pp. 260–287.
Ekeke et al, J. Ster. Biochem., 11(1979), 1597–1600.
Halliday et al, 96(2), 298–300, (1978).

Primary Examiner—Christine M. Nucker
Attorney, Agent, or Firm—Wenderoth, Lind & Ponack

[57] ABSTRACT

A biological sample containing an analyte, partly free and partly bound to natural binders, is incubated with a labelled specific binder for the analyte and a derivative of the analyte which does not react with the natural binders. Part of the labelled specific binder binds to the analyte derivative, the proportion depending on the free analyte concentration in the sample. The proportion is measured and used to determine the free analyte concentration. For example, the analyte may be thyroxine or cortisol, the labelled specific binder may be an antibody thereto, and the analyte derivative may be in the form of a solid matrix. The labelled specific binder should have an affinity for the analyte, expressed as a dissociation constant of the complex of the two, approximately equal to the concentration of free analyte in the sample.

16 Claims, No Drawings

ASSAY FOR THE FREE PORTION OF SUBSTANCES IN BIOLOGICAL FLUIDS

This application is a continuation of now abandoned application Ser. No. 748,702, filed June 25, 1985, which in turn is a continuation of now abandoned application Ser. No. 475,113, filed Mar. 14, 1983.

BACKGROUND

This invention relates to an assay for the free portion of organic substances or analytes that are present in biological fluids in both a form bound to protein (or other binding species present in the fluid) and in a non-bound or free form, the free and bound forms being in equilibrium with one another.

For most physiologically active substances that can be found jointly in both a free form and a protein-bound form in biological fluids such as blood, it is currently thought that it is the concentration of the free form that may control the physiological responses associated with those substances and may therefore be more significant clinically than in the concentration of total substance which includes both free (or unbound) and protein-bound substance.

European Patent Specification No. 26103 describes an assay method of this kind. The method involves causing the analyte and a labelled derivative thereof to compete for reaction with a specific binder for the analyte. The amount of the labelled derivative of the analyte which has become bound to the specific binder is then measured, and the measurement used to determine the concentration of the free analyte in the biological fluid. The amounts of labelled derivative and specific binder used are insufficient to substantially affect the aforesaid equilibrium. Also, the labelled derivative of the analyte is chosen to be substantially non-reactive with the natural binders in the biological fluid.

The method of the aforesaid European Patent Specification No.26103 is concerned with a competition immunoassay in which the labelled species is a version of the analyte. By contrast, the present invention is concerned with an assay in which the labelled species is a version of the specific binder for the analyte. In this respect, the assay of the present invention is more closely related to one-site immunometric assays.

Three kinds of assay may be summarised as follows:

(i) In a typical competition immunoassay, the reagents are the analyte (antigen), a version of the analyte tagged with a label (e,g. a radioactive atom), and an added specific binder (antibody for the analyte). The amount of specific binder used is insufficient for reaction with all the analyte and the labelled version thereof. The analyte and the labelled version thereof compete for reaction with the specific binder, and become bound thereto in proportions which depend on the concentration of the analyte in the assay sample. Then the bound portion of the labelled version of the analyte is separated from the non-bound portion, for which purpose the specific binder may be provided for example as a coating on solid particles or on the walls of the assay tube. The amount of labelled version of the analyte which is bound to the specific binder is inversely proportional to the concentration of the analyte in the assay sample.

(ii) In a typical one-site immunometric assay, the reagents are the analyte (antigen), a matrix-bound version of the analyte, and a specific binder (antibody) for the analyte. The amount of specific binder used is at least sufficient for reaction with all the analyte in the assay sample. In contrast to i), it is the specific binder which is tagged with a label (e.g. a radioactive atom). The analyte of the assay sample is reacted with the labelled specific binder. Then a sufficient amount of the matrix-bound analyte is added to react with excess labelled specific binder. Then the portion of the labelled specific binder bound to the matrix-bound analyte is separated from the portion not so bound. The amount of the specific binder which is bound to the matrix-bound analyte is inversely proportional to the concentration of the analyte in the assay sample. Immunometric assays are the subject of a review in British Medical Bulletin, 1974, pages 44 to 49.

(iii) Immunoassays have been described which are intermediate between (i) and (ii). See Journal of Steriod Biochemistry, 11, 1597–1600; and FEBS Letters, 96, 2, (Dec. 1978), 298–300. The reagents are, as in immunometric assay (ii), the analyte (antigen), a matrix-bound version of the analyte, and a labelled specific binder (antibody) for the analyte. The method, as in immunoassay (i), involves causing the analyte in the assay sample and the matrix-bound version thereof to compete for reaction with the labelled specific binder and to become bound thereto in proportions which depend on the concentration of the total analyte in the assay sample.

It is recognised that assays in which the specific binder is labelled are different from, and in some circumstances better than, assays in which a version of the analyte is labelled. For example, it may in some circumstances be easier to label an antibody than an antigen. Practical development of assays in which the specific binder is labelled have been delayed by the difficulty of providing labelled antibodies of sufficient purity. With the development of monoclonal antibodies, this difficulty is being overcome, and it is expected that such assays will in future achieve increasing importance.

This invention provides an assay in class (iii) which uses a labelled specific binder for the analyte, which assay is adapted to measure the free portion of an analyte present in a biological fluid in equilibrium with a portion of the analyte bound to one or more natural binders.

THE INVENTION

This invention provides a method of determining the concentration of the free portion of an analyte which is a member of a specific binding pair consisting of the analyte and a specific binder therefor, said free portion of the analyte being present in a biological fluid which also contains a portion of the analyte bound to one or more natural binders for the analyte, the bound and free portions of the analyte being in equilibrium with one another, by (a) forming a mixture of a sample of the biological fluid with an amount of a labelled version of a specific binder for the analyte and with a derivative of the analyte, the amount of said labelled specific binder being insufficient to substantially affect said equilibrium and said derivative of the analyte being substantially non-reactive with said natural binders;

(b) maintaining said mixture for a time to permit the free portion of the analyte and the derivative thereof to become bound to the labelled specific binder in proportions which depend on the concentration of the free portion of the analyte present in the sample;

(c) measuring the amount of the said labelled specific binder bound to the derivative of the analyte, and/or the amount of the said labelled specific binder not bound to the derivative of the analyte; and (d) using the measurement to determine the concentration of free analyte in the biological fluid.

THE ANALYTE

As regards the nature of the analyte, the method of the invention is of general applicability. Examples of classes of analytes to which the method may be applied are hormones, biochemical messengers, steroids, drugs, drug metabolites, polypeptides, proteins, vitamins, tumour antigens, toxins, alkaloids and mono-, di- and poly-saccharides.

The analyte is a member of a specific binding pair. When the analyte is a hapten or is itself immunogenic, the specific binder therefore may conveniently be an antibody to the analyte. But the invention is not confined to antibodies as specific binders, and is applicable to specific binding pairs generally, for example to the vitamin B12 - intrinsic factor system.

The free portion of the analyte is in equilibrium with the portion of the analyte bound to the natural binders in the biological fluid. Thus, if a small amount of free analyte is removed from the system (e.g. by becoming bound to its specific binder), then a corresponding small amount of analyte is freed by the natural binders in the biological fluid, so as to restore the equilibrium. Moreover, this process takes place in a time generally less than, and in any event not substantially greater than, the time taken for the assay.

THE LABELLED SPECIFIC BINDER

Use is made of a labelled version of the specific binder for the analyte. As noted above, the labelled specific binder is frequently an antibody to the analyte. It may have been labelled with any label which is used in immunoassays or immunometric assays. The most important groups of labels are radioactive atoms, enzymes or components of enzyme systems, and chemiluminescent and fluorescent groups. An enzyme assay involves the use of two or more components, e.g. an enzyme and its substrate, to generate a signal, and the specific binder may have been labelled with one or more of these components. Most usually, the specific binder will have been labelled with at least one radioactive atom, preferably one which emits gamma-radiation. Techniques for labelling antibodies and other specific binders are well known in the art and will not be described here.

The term "labelled, as used in this specification, needs some explanation. The term is used, not only in the narrow meaning of the previous paragraph, but in a somewhat broader sense. One way of performing steps a) and b) of the method of the invention is by the following steps:

(i) forming a mixture of a sample of the biological fluid with an amount of a specific binder for the analyte and with a derivative of the analyte, the amount of said specific binder being insufficient to substantially affect said equilibrium and said derivative of the analyte being substantially non-reactive with said natural binders;

(ii) maintaining said mixture for a time to permit the free portion of the analyte and the derivative thereof to become bound to the specific binder in proportions which depend on the concentration of the free portion of the analyte present in the sample;

(iii) separating the formed analyte derivative/ specific binder complex from the remainder of the reaction mixture, (iv) incubating said complex with an excess of an antibody (or other specific binder) for said specific binder, said antibody being tagged with a marker atom or group; and (v) washing the complex to remove antibody not bound thereto.

In this embodiment of the method of the invention, the specific binder is regarded as being "labelled" from the outset, by virtue of the portion of its molecule which is recognised in step iv) by the tagged antibody for binding purposes.

It has been found that the affinity of the labelled specific binder for the analyte, and for the analyte derivative, is an important factor in optimising an assay according to this invention. Affinity may conveniently be expressed in terms of dissociation constants, with respect to binding to the analyte, which are defined as the free analyte concentration multiplied by the free specific binder concentration divided by the analyte/-specific binder complex concentration. In the method of this invention, the dissociation constant of the labelled specific binder used should desirably be within a factor of about 20 times, preferably ten times, more or less than the free analyte concentration in the assay sample. If the affinity is too low, assay sensitivity is reduced; if too high, the assay has maximum sensitivity at free analyte concentrations below those found in practice. If the affinities of the labelled specific binder for the analyte and the analyte derivative are very different, these restrictions may not apply in quite the same way.

When the free analyte concentration in the assay sample is low, as is the case for example with thyroxine, the dissociation constant of the labelled specific binder should be correspondingly low. This requires the use of a specific binder having high affinity for the analyte.

Antisera are commonly mixtures of antibodies having different affinities for the antigen (analyte). In conventional competition immunoassays (for example conventional radioimmunoassay) it is the effect of the high-affinity antibodies in the mixture which is dominant, and the presence of substantial quantities of low-affinity antibodies is not deleterious. In the method of the present invention in which the antibodies are labelled, the presence of substantial quantities of low-affinity antibodies could be deleterious leading to a flat dose-response curve. It is therefore preferred that there should be used in the method of this invention antibodies which have suitable affinity and which are not mixed with antibodies having unsuitable (generally lower) affinities. Monoclonal antibodies are preferred.

Once the use of a particular labelled specific binder, having a desired affinity for the analyte, has been decided on, the amount of the labelled specific binder to be used is easily determined. If too little labelled specific binder is used, the assay will be sensitive only over a range of free analyte concentrations below those encountered in practice. Similarly, if too much labelled specific binder is used, the assay will be sensitive only at high free analyte concentrations.

It is, as previously stated, essential that the amount of labelled specific binder used should be insufficient to substantially affect the free-bound equilibrium of the analyte in the biological fluid. If a labelled specific binder is chosen which has a sufficiently high affinity for the analyte, then it is found that a suitable amount can be used for the assay without significantly affecting the free-bound analyte equilibrium. Put the other way round, the need to use a small amount of labelled specific binder, so as to avoid substantially affecting the free-bound analyte equilibrium, is one of the factors (but not the only factor) which dictates the use of a labelled specific binder having high affinity for the analyte.

THE ANALYTE DERIVATIVE

The derivative of the analyte is used to compete with the analyte for reaction with the labelled specific binder. It is necessary that this derivative of the analyte be substantially non-reactive with the natural binders for the analyte in the biological fluid. If substantial reaction were to occur, the free-bound equilibrium of the analyte in the biological fluid could be disturbed to such an extent that the assay would not give a true indication of the free analyte concentration. Additionally, a proportion of the analyte derivative would not be available to compete with the free analyte for reaction with the labelled specific binder, and this proportion would depend upon the amount and nature of the natural binders in the particular sample of biological fluid being assayed.

The analyte derivative has properties which permit quick and easy measurement of the proportion of the labelled specific binder which has become bound to the analyte. (For this purpose, the assumption is made that all labelled reagent not bound to the analyte becomes bound to the analyte derivative). In this connection there are two categories of assay:

(i) Homogeneous assays. In these, the fraction of the labelled specific binder bound to the analyte derivative is not separated from the fraction of the labelled specific binder not so bound prior to measurement of the signal emitted by the label. This is practicable and may be advantageous for enzyme, chemiluminescent and fluorescent assay systems. But it is necessary that the signal emitted by the label of labelled specific binder which is bound to the analyte derivative be in some way different from the signal emitted by the label of labelled specific binder which is bound to the analyte. In this case therefore, the analyte derivative must be chosen to modify the signal emitted by the fraction of the labelled specific binder which becomes bound to it.

(ii) Heterogeneous assays. In these the fraction of the labelled specific binder bound to the analyte derivative is separated from the fraction of the labelled specific binder bound to the analyte prior to measurement of the signal emitted by one or other fraction. Radioassay systems are normally heterogeneous, and other assay systems may be also. In this case, the analyte derivative serves as a means for separation. The analyte derivative is therefore generally used, either in the solid phase, or in a form which is readily transferred from the liquid to the solid phase.

For heterogeneous assays, the requirements for the analyte derivative may be summarised:

(a) it must be readily separable, after reaction with the labelled specific binder, from the liquid assay medium;

(b) it must react with the labelled specific binder; and (c) it must be substantially non-reactive with the natural binders for the analyte in the biological fluid.

The property (a), that the analyte derivative be readily separable, after reaction with the labelled specific binder, from the liquid assay medium, may be achieved in various ways:

(i) The analyte may be bound to a matrix, e.g. in the form of solid particles or of the assay tube itself. Then, separation is easily achieved by centrifuging or merely decanting and washing.

(ii) The analyte derivative may include a different hapten or antigen. An antibody to the different hapten or antigen, which is non-reactive towards natural binders for the analyte, can be used in a matrix-bound form or otherwise to achieve the desired separation.

(iii) The analyte derivative may include a chelating agent or to some other chemically reactive species which is easily precipitated out of solution, or bound to an absorbent, for example an ion-exchange resin, or extracted with an organic solvent.

(iv) The analyte derivative may include biotin. Separation can then be achieved by the use of avidin or streptavidin, e.g. in a matrix bound form.

It will be apparent that the analyte is modified in some way to form the analyte derivative. This modification may be a chemical modification; or it may amount to no more than binding the analyte to a matrix. The modification must, however, not destroy the natural affinity of the analyte for its specific binder, and this must be true even in the presence of the natural binders in the biological field. With this in mind, modification or binding of the analyte should normally be effected at some part of the analyte molecule that is not recognised for the purpose of binding by the specific reagent. There is also the possibility that the analyte may lose affinity for its specific binder on becoming bound to a solid matrix. This problem may be avoided by providing a long bridge between the analyte and the matrix.

The property (c), that the analyte derivative be substantially non-reactive with the natural binders for the analyte, may also be achieved in various ways:

(i) Binding of the analyte to a matrix may be effected through some part of the analyte molecule that is recognised for the purpose of binding by the natural binders.

(ii) Modification of the analyte may be effected at some part of the analyte molecule that is recognised for the purpose of binding by the natural binders.

(III) The surface of a matrix bearing the analyte or a derivative thereof may be modified by the attachment of groups which repel or otherwise hinder the action of the natural binders.

(iv) Depending on the nature of the protein-binding sites, the bridge between the analyte and the matrix may be arranged to be so short that the analyte is protected by proximity to the matrix (the bridge nevertheless being long enough to permit reaction of the analyte with the labelled specific binder).

The choice of an analyte derivative having this combination of features will depend on the nature of the analyte. Factors affecting the choice when the analyte is a thyroid hormone or a steroid are discussed below.

The amount of analyte derivative used is related to the amount of labelled specific binder. If the molar ratio of analyte derivative concentration to labelled specific binder concentration is very large, then the proportion of label bound to the analyte derivative will always be close to 100%. Correspondingly, if the ratio is very small, then the proportion will always be close to 0%. The molar ratio should preferably be in a range of about 1 to 50, preferably about 10.

ASSAY CONDITIONS

Suitable conditions for performing the method of this invention, including time and temperature of incubation, and pH of the assay medium, may be readily determined from a knowledge of conventional assays for the analyte. The reactants may be mixed in different ways:

(i) The labelled specific binder and the analyte derivative are added simultaneously or consecutively to the assay sample, whereby the free analyte and the analyte derivative compete for reaction with the labelled specific binder.

(ii) The labelled specific binder is added to the assay sample in a form bound to the analyte derivative. Some of the labelled specific binder is freed from the complex and becomes bound to the free analyte.

As noted above, the labelled specific binder is often an antibody to the analyte. It is known that antibodies are divalent. It might be thought that a problem would arise because a molecule of antibody would react with both a molecule of the analyte and a molecule of the analyte derivative. If this were to happen to any great extent, this would reduce the sensitivity of the assay. However, this problem, which is theoretically common to all one-site immunometric assays does not appear to arise to any significant degree in practice. The problem can be avoided, if necessary, by rendering the antibody monovalent e.g. by splitting the antibody into two smaller monovalent molecules (e.g. Fab fragments).

The method of this invention is envisaged mainly as an equilibrium approach to assay. However, some reactions may be rather slow to reach equilibrium, particularly where the analyte is a large molecule and/or where the analyte derivative is bound to an insoluble matrix. In such cases the method can be adapted to a kinetic or non-equilibrium approach.

In heterogeneous assays, separation of the fraction of labelled specific binder bound to the analyte usually involves separation of a solid from a liquid phase, and this may be effected by conventional means, e.g. centrifuging. Measurement of the signal emitted by the bound and/or the unbound fraction may also be effected by conventional means.

It is to be recognized that at equilibrium the distribution of the analyte derivative between the labelled specific binder and elsewhere is determined by the amounts of natural binders and labelled specific binder present, by their affinity constants for the analyte and its derivative, and by the amounts of analyte and its derivative present. While it might be theoretically possible to calculate the amount of analyte in the free form from a knowledge of the amount of analyte derivative bound to the labelled specific binder and the other relevant data, this is not a practicable procedure, and recourse must be made to a standard assay procedure, namely, the use of a "dose-response curve" or "standard curve". In this procedure, a number of standard sera, of known free analyte content (determined, for example, by equilibrium dialysis), spanning the required working range of the method, are measured in the procedure. The results are plotted graphically and unknown samples are read off against the curve. The actual amounts of sample, labelled specific binder and analyte derivative are optimized to give a dose response curve of adequate slope (and hence of adequate assay sensitivity) over the desired working range of the assay. The process of optimizing an assay is one familiar to those who practice radioimmunoassay and related procedures, and can be carried out using iterative computer methods as described below.

COMPUTER OPTIMISATION

For many analytes that are found in both free and bound forms in biological fluids, the number of natural binders for a given analyte is two or more. Where the binding of two or more of the proteins is reversible, the chemical equilibrium between the free analyte, unbound natural binders and analyte bound to each of the natural binders, is both complex and interactive. The Law of Mass Action provides a convenient method for describing the component parts of this total equilibrium; these in turn can be used to build up a full description of the complete complex equilibrium.

For each natural binder (total concentration $[P_j]$) an equilibrium between the free analyte $[F_1]$, bound analyte $[B_{1j}]$ and unbound protein $([P_j]-[B_{1j}])$ is established having an equilibrium constant $K_{1j}$ which may be represented as follows:

$$K_{1j} = \frac{[B_{1j}]}{[F_1]\,([P_j] - [B_{1j}])}$$

In the general case wherein the free analyte coexists with analyte bound to each of n natural binders the free and bound forms are related to the total analyte $[T_1]$ in the following manner:

$$[T_1] = [F_1] + \sum_{j=1}^{j=n} [B_{1j}]$$

Using the two equations above the complete equilibrium between the free analyte and the various bound forms of the analyte can be described in terms of the total concentration of each natural binder, the equilibrium constant for the analyte with each natural binder and the total concentration of the analyte:

$$\text{Total analyte } [T_1] = [F_1] + \sum_{j=1}^{j=n} \left[ \frac{K_{1j}[P_j]\,[F_1]}{1 + K_{1j}[F_1]} \right]$$

Each $j^{th}$ term in the summation series describes the concentration of analyte bound to the $j^{th}$ protein These techniques can be extended to describe the binding of both analyte and analyte derivative to the natural binders and the labelled specific binder at equilibrium in the present invention.

Desirably, but not necessarily, the labelled specific binder will be an antibody specific to both the analyte and the analyte derivative, its concentration being $[P_{(n+1)}]$. Whilst the equilibrium constant $K_{2(n+1)}$ for the analyte derivative with respect to the labelled specific binder may be the same as that $K_{1(n+1)}$ for the analyte with respect to the specific binder, it is not always necessary for this to be so. If the free analyte derivative is described by $[F_2]$, the distribution of analyte between the natural binders and the labelled specific binder is given by the following:

$$[T_1] = [F_1] + \sum_{j=1}^{j=n} \left[ \frac{K_{1j}[P_j]\,[F_1]}{1 + K_{1j}[F_1]} \right] + \left[ \frac{K_{1(n+1)}[P_{(n+1)}]\,[F_1]}{1 + K_{1(n+1)}[F_1] + K_{2(n+1)}[F_2]} \right] \quad (1)$$

If the situation wherein the analyte derivative (total concentration [$T_2$]) does not have any residual binding to the natural binders, the distribution of analyte derivative between free and labelled specific binder bound forms is as follows:

$$[T_2] = [F_2] + \left[\frac{K_{2(n+1)}[P_{(n+1)}][F_2]}{1 + K_{1(n+1)}[F_1] + K_{2(n+1)}[F_2]}\right] \quad (2)$$

If the equilibrium constants of the natural binders and the labelled specific binder together with the total concentrations of analyte derivative, natural binders and labelled specific binder are known, it is possible to estimate the amounts of labeled specific binder bound to the analyte derivative at equilibrium in the assay by solving the simultaneous equations (1) and (2) to obtain estimates [$F_1$] and [$F_2$] which are then used in equation (2) to obtain a direct estimate of labelled specific binder so bound. These calculations may be conveniently carried out using iterative computer methods familiar to those who practice numerical analysis.

Desirably, but not necessarily, the analyte derivative, in the assay, will be non-binding to the natural binders. In the event that weak residual binders of the analyte derivative occurs, with an equilibrium constant $K_{2j}$, to any of the natural binders, the distribution of analyte derivative between the free form and the various bound forms at equilibrium in the assay will be as follows:

$$[T_2] = (F_2) + \left[\frac{K_{2(n+1)}[P_{(n+1)}][F_2]}{1 + K_{1(n+1)}[F_1] + K_{2(n+2)}[F_2]}\right] + \sum_{j=1}^{j=n}[K_j[P_j][F_2]] \quad (3)$$

Each $j^{th}$ term in the summation describes the weak residual binding of analyte derivative to the $j^{th}$ protein.

Equation (3) then replaces equation (2) in all respects when used in estimating the amount of labelled specific binder bound to the analyte derivative.

These calculations are especially useful in optimising assays utilising this invention, particularly in respect of determining the quality and quantities of both analyte derivative and labelled specific binder required.

By the use of computer calculation methods described above, it is possible by varying the estimate for the equilibrium constants for the labelled specific binder and the concentrations of both the analyte derivative and the labelled specific binder, to determine optimal ranges for all of these consistent with; insignificant alteration of the free-bound analyte equilibrium; a dose response curve of adequate slope (and hence adequate assay sensitivity); and negligible distortion of the measured free analyte estimates arising out of residual weak binding of analyte derivative to the natural binders. The results of computer calculations for three specific analytes are set out in Examples 2, 3 and 4.

APPLICATION TO THYROID HORMONES

This section discusses some of the factors, including particularly the design of a matrix-bound analyte derivative, in setting up a radioassay according to the invention for thyroid hormones. These have the formula:

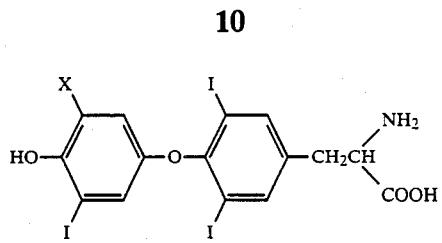

X is I in thyroxine (T4).
X is H in tri-iodothyronine (T3).

T4 is transported in the blood stream of human beings largely (99.98%) bound to three naturally occurring T4- binding proteins, thyroxine-binding globulin (TBG), thyroxine-binding pre-albumin (TBPA) and albumin (ALB). The percentage of T4 bound to each of these is approximately 70%, 20 to 25% and 5 to 10% respectively. In designing a matrix-bound T4 derivative for this particular assay it is important that the binding of the derivative to TBG and TBPA and Alb in the assay is zero or very much less than the binding of the derivative to the labelled specific binder used in the assay.

It is known, e.g. from European Patent Specification No.26103, that the binding of T4 to natural binders is very dependent on the carboxylic acid and the amino group of the amino acid end of the T4 molecule. In the case of T4 derivatives that have had either or both of these groups removed or chemically modified to prevent them ionizing in the usual way, or modified by attachment of bulky chemical groups, binding of the derivatives to the natural binders is substantially reduced with respect of T4. On the other hand the binding strength of these derivatives with antisera raised to an immunogen consisting of such a derivative coupled via the amino acid end of the T4 molecule to a large protein such as bovine serum albumin, is often comparable to that of T4 itself.

One of the reagents required for the assay is a radioactively labelled antibody to T4. T4 is not itself immunogenic, but it may be coupled to bovine serum albumin and used in that form to raise antibodies in sheep or rabbits. The antibodies are then purified and labelled with a radioactive atom such as iodine-125. Alternatively a hybridoma technique for raising monoclonal antibodies may be used. The techniques for all these operations are well-known and will not be described here.

The other reagent required is a derivative of T4. This must be readily separable, after reaction with the labelled antibody, from the liquid assay medium. This property may be achieved in various ways, as noted above in the general description:

(i) The T4 may be bound to a matrix, e.g. in the form of solid particles or of the assay tube itself.

(ii) The T4 may be bound to different antigen.

(iii) The T4 may be bound to a chelating agent or to some other chemically reactive species which is easily precipitated out or otherwise removed from aqueous solution.

It is also necessary that this T4 derivative should bind strongly to the labelled T4 antibody. Since T4 antibodies recognise for the purpose of binding the left hand end of the T4 molecule (as shown above) the T4 should be bonded, e.g. to a matrix, by some group at the right hand end of the molecule, e.g. through the carboxylic acid or amino group. There is a possibility that the T4 may lose immunoreactivity on becoming bound to a matrix. This problem may be avoided by providing a long bridge between the matrix and the T4.

A third requirement of the T4 derivative is that it should be substantially non-reactive with the natural binders (particularly TBG and TBPA) in the biological fluid. This property may be achieved in various ways:

(a) It is known that TBG and TBPA mainly recognise for the purpose of binding the amino acid end of the T4 molecule. It may therefore be sufficient to suppress reactivity with these binders to bind a matrix to the T4 through its carboxylic acid or amino group. Such material has been described (Archives of Biochemistry and Biophysics, 135, 304–310 (1969) and is available commercially.

The T4 would normally be bound through one of these groups in any event, but further steps may need to be taken to suppress reaction with natural binders, as noted in (b) and (c).

(b) The T4 derivative may be made by modifying the structure of T4 in one or more of the following ways:

1. Modifying the charge of the carboxylic acid and the terminal amino group of the alanine side chain of T4.

2. Adding a bulky group to either or both of the terminal carboxylic acid or amino groups.

3. Preparing derivatives of T4 with the D-configuration rather than the naturally occurring L-configuration.

European Patent Specification No. 26103 contains a general discussion and specific example of T4 derivatives which have been modified to suppress binding to TBG and TBPA.

(c) The surface of a matrix bearing T4 or a derivative of T4 may be modified by the attachment of groups which repel TBG, TBPA, and Alb, but nevertheless permit adequate binding of the antibody to the T4 or T4 derivative.

Similar considerations to those set out above can be used to design reagents for the assay of other analytes.

For example, tri-iodothyronine is present in the bloodstream mainly bound to the same three binding proteins (TBG, TBPA and Alb) as bind T4. A labelled antibody to tri-iodothyronine, and a matrix-bound triiodothyronine derivative can be prepared as for T4.

APPLICATION TO CORTISOL

The steroid hormone cortisol is found in blood plasma both in the free form (8%) and also bound (92%) to the naturally occurring plasma proteins corticosteroid binding globulin (known also as CBG or transcortin) and serum albumin. It is known that binding of cortisol (and similarly progesterone) to CBG takes place through the A and B rings, which it is believed fit into a cleft in the CBG molecule.

An important paper relating to steroid is: "Steroid-Protein Interactions. Influence of Steroid Structure and Temperature on the Binding of Steroids to Guinea Pig Corticosteroid-Binding Globulin".
Mickelson K. E. and Westphal U.
Biochemistry 1980, 19, 585–590.

The paper indicates, for example, that the addition of a 20 beta-hydroxyl group to cortisol reduces its affinity constant (Ka) to corticosteroid binding globulin (CBG) by a factor of about 350, that addition of a 9 alpha-fluoro-group to cortisol acetate reduces Ka by a factor of about 200 and that addition of a 5 beta-hydroxyl group to progesterone reduces Ka by a factor of about 100.

The comments for cortisol apply also to the steroids progesterone, oestradiol and testosterone. It is well-known that progesterone binds to CBG through its A and B rings in the same manner as cortisol. Similarly, the sex hormones testosterone and oestradiol bind strongly to the protein sex hormone binding globulin, and this binding is relieved to be through the A and B rings.

Use can be made of this known information to design matrix-bound analyte derivatives which do not bind significantly to naturally occurring binders in the biological fluid.

The following Examples illustrate the invention.

EXAMPLE 1

Immunoradiometric Assay for Free Thyroxine

The solid phase derivative of the ligand was a succinylated amino ethyl derivative of polyacrylamide of particle size 1–3 microns linked to L-Thyroxine via the amino group by standard carbodiimide techniques. The immunogenic concentration of matrix bound T4 used in the working assay was $1 \times 10^{-9}$M.

The buffer used throughout contained 7.8 g/l NaH$_2$PO$_4$.2H$_2$O, 9.0 g/l NaCl, 5.0 g/l BSA and 1 g/l NaN$_3$.

The first antibody employed was rabbit antiserum to T4 used at 1 in 4000 dilution. The labelled second antibody used was anti-rabbit whole antibody from donkey, $^{125}$I labelled to a specific activity of 20 $\mu$Ci/g and diluted for use in the system to approximately 100,000 cpm per 100 microliters.

20 microlitres of a serum sample was mixed with 100 microliters of rabbit anti-T4 first antibody and 100 microliters of solid phase dilution, and the mixture incubated at 37° for one hour. Then 500 microliters of buffer were added and the reaction mixture centrifuged and the supernatant liquid decanted. This washing step was repeated prior to the addition of 100 microliters of anti-rabbit $^{125}$I labelled second antibody. The reaction mixture was incubated for a further half hour at 37° C. and the two washing steps repeated. The radioactivity of the precipitate was then measured.

| FT4 ng/dl previously determined by reference method | Radioactive cpm in precipitate |
| --- | --- |
| 0 | 705 |
| 1.0 | 629 |
| 2.0 | 597 |
| 5.2 | 446 |
| 10.5 | 272 |

The computer optimisation methods described above have been applied to the immunometric assays of the free portions of three hormones.

EXAMPLE 2

Thyroxine (T4) is transported in the blood stream of human beings largely bound to the three naturally occurring proteins TBG, TBPA and Albumin. The percentage of T4 bound to each of these is approximately 70%, 20–25% and 5–10% respectively. Free thyroxine concentrations are typically in the region of $1.7 \times 10^{-11}$M and amount to some 0.02% of the total T4. With regard to the equilibrium constants for T4 with respect to each of the natural binders an article of interest here is:

H. P. Prince and D. B. Ramsden, Clinical Endocrinology, and, (1977) pp 307–324

A labelled antibody with an equilibrium dissociation constant in respect of T4 of $1\times 10^{-11}$M was found to be suitable for the immunoradiometric assay of free thyroxine, using a matrix-bound T4 derivative concentration of $1\times 10^{-11}$M and a labelled antibody concentration of $1\times 10^{-12}$M.

EXAMPLE 3

Testosterone is transported in the blood stream of human beings largely bound to two naturally occurring proteins SHBG (TeBG) and Albumin. In adult males about 55% of testosterone is bound to SHBG (TeBG) and 43% is bound to albumin with some 2% of testosterone being in the free form. In adult females some 79% of testosterone is bound to SHBG (TeBG), 20% is bound to albumin and approximately 1% is in the free form.

Free testosterone concentrations are typically in the region of $4\times 10^{-10}$M for adult males and $2\times 10^{-11}$M for adult females. With regard to the equilibrium constants for testosterone with respect to each of the natural binders, articles of interest here are:

(a) M. J. Iqbal and M. W. Johnson, J. Steroid Biochem., 10 (1979) pp 535–540

(b) R. G. Smith, P. K. Besch, B. M. T. Dill and V. C. Buttram, Fertility and Sterility, 31 (1979) pp 513–517

A labelled antibody with an equilibrium dissociation constant in respect of testosterone of $1\times 10^{-10}$M was found to be suitable for the immunoradiometric assay of free testosterone, using a matrix-bound testosterone derivative concentration of $1\times 10^{-10}$M and a labelled antibody concentration of $1\times 10^{-11}$M.

EXAMPLE 4

Cortisol is transported in the blood stream of human beings largely bound to two naturally occurring proteins, transcortin (CBG) and Albumin. The percentage of cortisol bound to these is approximately 77% and 15% respectively with some 8% of cortisol being present in the free form. Free cortisol concentrations may typically be in the region of $6\times 10^{-8}$M, although there are significant diurnal variations. With regard to equilibrium constants for cortisol with respect to each of the natural binders an article of interest here is:

I. Jerkunica, J. Sophianopoulos and D. Sgoutas, Clin. Chem., 26 (1980) pp 1734–1737

A labelled antibody with an equilibrium dissociation constant $1\times 10^{-7}$M was found to be suitable for the immunoradiometric assay of free cortisol, using a matrix-cortisol derivative concentration of $1\times 10^{-7}$M and a labelled antibody concentration of $1\times 10^{-8}$M.

What is claimed is:

1. A method of determining the concentration of the free portion of an analyte which is a member of a specific binding pair consisting of the analyte and a specific binder therefor, said free portion of the analyte being present in a biological fluid which also contains a portion of the analyte bound to one or more natural binders for the analyte, the bound and free portions of the analyte being equilibrium with one another, by
   (a) forming a mixture of a sample of the biological fluid with an amount of a labelled version of a specific binder for the analyte and with a derivative of the analyte, the amount of said labelled specific binder being insufficient to substantially affect said equilibrium and said derivative of the analyte being substantially non-reactive with said natural binders;
   (b) maintaining said mixture for a time sufficient to permit the free portion of the analyte and the derivative thereof to become bound to the labelled specific binder in proportions which depend on the concentration of the free portion of the analyte present in the sample;
   (c) separating the analyte derivative bound to the specific binder from said mixture;
   (d) measuring the amount of the said labelled specific binder bound to the derivative of the analyte and/or the amount of the said labelled specific binder not bound to the derivative of the analyte; and
   (e) using the measurement to determine the concentration of free analyte in the biological fluid, and
wherein the analyte derivative is bound to a solid matrix prior to step (c) and wherein the labelled binder has a dissociation constant, with respect to its binding to the analyte, within a factor of 10 times more or less than the free analyte concentration.

2. A method as claimed in claim 1, wherein the specific binder is an antibody to the analyte.

3. A method as claimed in claim 1, wherein the label for the specific binder is selected from the group consisting of radioactive atoms, enzymes or components of enzyme systems, and chemiluminescent and fluorescent groups.

4. A method as claimed in claim 1, wherein steps (a), (b) and (c) are performed by:
   (i) forming a mixture of a sample of the biological fluid with an amount of a specific binder for the analyte and with a derivative of the analyte, the amount of said specific binder being insufficient to substantially affect said equilibrium and said derivative of the analyte being substantially non-reactive with said natural binders;
   (ii) maintaining said mixture for a time to permit the free portion of the analyte and the derivative thereof to become bound to the specific binder in proportions which depend on the concentration of the free portion of the analyte present in the sample.
   (iii) separating the formed analyte derivative/specific binder complex from the remainder of the reaction mixture.
   (iv) incubating said complex with an excess of an antibody or other specific binder for said specific binder, said antibody being tagged with a marker atom or group; and
   (v) washing the complex to remove antibody not bound thereto.

5. A method as claimed in claim 1, wherein in the analyte derivative the analyte is bound to a solid matrix for easy separation from the reaction mixture.

6. A method as claimed in claim 1, wherein the analyte derivative includes a different hapten or antigen in a form capable of binding to an antibody to said different hapten or antigen.

7. A method as claimed in claim 1, wherein the analyte derivative includes biotin in a form capable of binding to avidin or streptavidin.

8. A method as claimed in claim 1, wherein, in the analyte derivative, the analyte is bound to a solid matrix through a part of the analyte molecule that is recognised for the purpose of binding by the natural binders.

9. A method as claimed in claim 1, wherein, in the analyte derivative, the analyte is bound to a solid matrix, to the surface of which are attached groups which repel or otherwise hinder the action of the natural binders.

10. A method as claimed in claim 1, wherein the molar ratio of analyte derivative concentration to labelled specific binder concentration is in a range of about 1 to 50

11. A method as claimed in claim 1, wherein step (e) is performed by measuring a set of standards containing different known concentrations of free analyte, plotting the measurements obtained on a graph of signal against free analyte concentration, and determining the free analyte concentration of the assay sample from the graph.

12. A method as claimed in claim 1, wherein the analyte is thyroxine or cortisol.

13. A method as claimed in claim 1, wherein the analyte is testosterone.

14. An assay kit for determining the concentration of the free portion of an analyte present in a biological fluid which also contains a portion of the analyte bound to one or more natural binders for the analyte the bound and free portions of the analyte being in equilibrium with one another, comprising:
  (a) a supply of a derivative of the analyte which is substantially non-reactive with the natural binders; and
  (b) a supply of a labelled specific binder for the analyte and the analyte derivative, wherein said labelled binder has a dissociation constant, with respect to its binding to the analyte, within a factor of 10 times more or less than the expected concentration of the free analyte in the assay sample.

15. An assay kit as claimed in claim 14, wherein the analyte is thyroxine or cortisol.

16. An assay kit as claimed in claim 14, wherein the analyte derivative comprises the analyte bound to a solid matrix and the specific binder is labelled with a radioactive atom.

* * * * *